United States Patent [19]
dePinto

[11] Patent Number: 5,259,387
[45] Date of Patent: Nov. 9, 1993

[54] ECG MUSCLE ARTIFACT FILTER SYSTEM
[75] Inventor: Victor M. dePinto, Kirkland, Wash.
[73] Assignee: Quinton Instrument Company, Seattle, Wash.
[21] Appl. No.: 756,933
[22] Filed: Sep. 9, 1991
[51] Int. Cl.$^5$ .......................................... A61B 5/0402
[52] U.S. Cl. ..................................... 128/696; 128/703
[58] Field of Search ............... 128/696, 708, 703, 704, 128/901

[56]  References Cited
U.S. PATENT DOCUMENTS

| | | | |
|---|---|---|---|
| 3,569,852 | 3/1971 | Berkovits | 330/132 |
| 3,581,219 | 5/1971 | Alexander | 328/168 |
| 3,590,811 | 7/1971 | Harris | 128/2.06 |
| 3,767,939 | 10/1973 | Chamran et al. | 307/251 |
| 3,902,479 | 9/1975 | Chaumet | 128/2.06 |
| 3,903,874 | 9/1975 | Shakespeare | 128/2.06 |
| 3,905,364 | 9/1975 | Cudahy et al. | 128/2.06 |
| 3,927,663 | 12/1975 | Russell et al. | 128/2.06 |
| 3,968,430 | 7/1976 | Maas | 324/77 B |
| 4,000,461 | 12/1976 | Barber et al. | 324/102 |
| 4,157,711 | 6/1979 | Yotam et al. | 128/708 |
| 4,161,945 | 7/1979 | Grossman | 128/696 |
| 4,192,318 | 3/1980 | Dam et al. | 128/708 |
| 4,213,467 | 7/1980 | Stulen et al. | 128/733 |
| 4,216,780 | 8/1980 | Rubel et al. | 128/699 |
| 4,243,045 | 1/1981 | Maas | 128/696 |
| 4,408,615 | 10/1983 | Grossman | 128/696 |
| 4,448,202 | 5/1984 | Wajszczuk et al. | 128/709 |
| 4,453,218 | 6/1984 | Sperinde et al. | 364/416 |
| 4,457,315 | 7/1984 | Bennish | 128/704 |
| 4,458,691 | 7/1984 | Netravali | 128/705 |
| 4,458,692 | 7/1984 | Simson | 128/705 |
| 4,478,224 | 10/1984 | Bailey | 128/706 |
| 4,494,551 | 1/1985 | Little, III et al. | 128/696 |
| 4,527,567 | 7/1985 | Fischler et al. | 128/419 PT |
| 4,537,196 | 8/1985 | Phillipps et al. | 128/630 |
| 4,537,200 | 8/1985 | Widrow | 128/696 |
| 4,617,938 | 10/1986 | Shimoni et al. | 128/708 |
| 4,646,258 | 2/1987 | Miodownik | 364/825 |
| 4,664,116 | 5/1987 | Shaya et al. | 128/419 PT |
| 4,751,931 | 6/1988 | Briller et al. | 128/700 |
| 4,781,201 | 11/1988 | Wright et al. | 128/671 |
| 4,793,361 | 12/1988 | DuFault | 128/696 |
| 4,832,041 | 5/1989 | Wang et al. | 128/697 |
| 4,887,609 | 12/1989 | Cole, Jr. | 128/696 |
| 5,002,064 | 3/1991 | Allain et al. | 128/710 |

FOREIGN PATENT DOCUMENTS 1-227739  9/1989  Japan .
1-227740  9/1989  Japan .
8909514   5/1989  PCT Int'l Appl. .

Primary Examiner—William E. Kamm
Assistant Examiner—Scott M. Getzow
Attorney, Agent, or Firm—Andrew J. Beck; Montgomery W. Smith; Curtis D. Kinghorn

[57] ABSTRACT

A filter system for removing small amplitude, high frequency signals such as muscle artifact signals from an ECG signal is provided. The filter system includes a low pass filter with variable cutoff frequencies, an electronic delay and a system for detecting the R wave in the ECG signal and determining the variable cutoff frequency in response to the detection of the R wave. A digitized input ECG signal is simultaneously presented to the electronic delay and the system for detecting the R wave. During the portion of the ECG signal exclusive of the QRS complex, the filter is operated at a low cutoff frequency to filter the muscle artifact signals for a maximum smoothing effect. At a time slightly prior to the on set of the QRS complex, the cutoff frequency is rapidly incrementally increased to a higher cutoff frequency to pass the QRS complex with a minimum reduction of amplitude of the QRS signal. At the end of the QRS signal, the cutoff frequency of the filter is rapidly incrementally returned to the low cutoff frequency.

17 Claims, 5 Drawing Sheets

FIR FILTER $$A = \left( \sum_{i=0}^{12} C_i \right)^{-1}$$

COEFFICIENT TABLE

| ZONE | $C_0$ | $C_1$ | $C_2$ | $C_3$ | $C_4$ | $C_5$ | $C_6$ | $C_7$ | $C_8$ | $C_9$ | $C_{10}$ | $C_{11}$ | $C_{12}$ | A | f₃dB Hz |
|---|---|---|---|---|---|---|---|---|---|---|---|---|---|---|---|
| $r_0$ | 0 | 0 | 0 | 0 | 0 | .367 | 1 | .367 | 0 | 0 | 0 | 0 | 0 | $\frac{1}{1+2\times.367}$ | 100 |
| $r_1$ | 0 | 0 | 0 | 0 | 0 | 1 | 1 | 1 | 0 | 0 | 0 | 0 | 0 | $\frac{1}{3}$ | 77.6 |
| $r_2$ | 0 | 0 | 0 | 0 | 1 | 1 | 1 | 1 | 1 | 0 | 0 | 0 | 0 | $\frac{1}{5}$ | 45 |
| $r_3$ | 0 | 0 | 0 | 1 | 1 | 1 | 1 | 1 | 1 | 1 | 0 | 0 | 0 | $\frac{1}{7}$ | 31.9 |
| $r_4$ | 0 | 0 | 1 | 1 | 1 | 1 | 1 | 1 | 1 | 1 | 1 | 0 | 0 | $\frac{1}{9}$ | 24.7 |
| $r_5$ | 1 | 1 | 1 | 1 | 1 | 1 | 1 | 1 | 1 | 1 | 1 | 1 | 1 | $\frac{1}{13}$ | 17.1 |

ECG MUSCLE ARTIFACT FILTER SYSTEM

BACKGROUND OF THE INVENTION

1. Field of the Invention

The instant invention relates to a filter system for removing small amplitude, high frequency signals such as muscle artifact signals from an ECG signal, and more particularly relates to a filter system having a low pass filter with variable cutoff frequencies which cutoff frequencies are implemented in response to the detection of a QRS complex in an ECG signal.

2. Background of the Invention

A common problem in electrocardiography is the contamination of the ECG signal with artifacts from skeletal muscle tremors, which appear on the ECG signal as rapid, wavy deflections. These deflections render the electrocardiogram difficult to read. A common solution for the muscle artifact problem has been to pass the ECG signal through a low pass filter having a low cut-off frequency, typically approximately 25 Hz. Since muscle artifact signals typically have significant energy at frequencies higher than 25 Hz, the low pass filter effectively reduces the muscle artifact signal. However, the low pass filter has the disadvantage of reducing the amplitude of the QRS complex because the high frequency components of the ECG signal necessary to describe the relatively high peaks of the QRS signal are also removed as the ECG signal passes through the low pass filter.

SUMMARY OF THE INVENTION

The input ECG signal is passed through a low pass filter having variable cut-off frequencies. During the portion of the ECG signal exclusive of the QRS complex, the filter is operated at a low cut-off frequency to filter the muscle artifact signals for a maximum smoothing effect. At a time slightly prior to the onset of the QRS complex, the cut-off frequency is incrementally increased to a higher cut-off frequency to pass the QRS complex with a minimum reduction of amplitude of the QRS signal. At the end of the QRS signal, the cut-off frequency of the filter is incrementally returned to the low cut-off frequency.

A system to determine the variable cut-off frequency of the low-pass filter is provided. In the system, because the R wave of the QRS complex typically has the largest amplitude and corresponding slope of any portion of the ECG signal, the R wave is detected and used to direct when the cut-off frequency of the low pass filter is to be altered.

The input ECG signal is simultaneously presented to an electronic delay and to the system which determines the variable cut-off frequency in response to the detection of the R wave. The output of the electronic delay is in turn connected to the variable frequency low-pass filter which is directed by the R wave detection system to determine the variable cut-off frequency. Upon detection of the R wave, the cut-off frequency of the low pass filter, under the direction of the system for determining the variable cut-off frequency, is incrementally altered to higher and higher cut-off frequencies until the maximum cut-off frequency is reached. The filter remains at this maximum cut-off frequency for a time slightly longer than the time length of the QRS signal so that the QRS complex may pass through the filter while it is operating at its maximum cut-off frequency. Thereafter, the filter incrementally returns to its lowest cut-off frequency.

Since the filter is directed to move to the higher cut-off frequency only upon the detection of the R wave, which is located in the middle of the QRS complex, the original input ECG signal is electronically delayed for a time sufficient to allow the R wave of the input ECG signal to be centered in the time span during which the variable cut-off frequency low pass filter is operating at its highest cut-off frequency. After passing through the delay circuitry, the ECG signal is passed to the variable cut-off frequency low pass filter for filtering. In this way, the filter is directed to operate at its highest low pass frequency during the time the QRS complex passes through the filter whereafter the filter is directed to operate at its lowest low pass frequency during the passing of the part of the ECG signal between QRS complexes. This system maximizes the reduction of muscle artifact signals without greatly reducing the amplitude of the QRS complex.

It is therefore an object of the instant invention to provide a filter system for filtering muscle artifact signals which maximizes the filtering of the muscle artifact signals during part of the ECG signal where the QRS complex is not present, yet which passes the QRS signal with a minimum of distortion due to filtering.

It is a further object of the instant invention to provide a filtering system which may be readily implemented on a digital processing system.

It is a further object of the instant invention to provide a filter system which may be easily implemented with other filter systems in an ECG monitoring system.

Finally, it is an object of the instant invention to provide a filtering system which is relatively simple and easy to make and use.

These and other objects of the instant invention will become clear from the description contained herein and more particularly with reference to the following detailed description where like elements are referred to by like reference numbers.

DETAILED DESCRIPTION OF THE INVENTION

Figure 1:
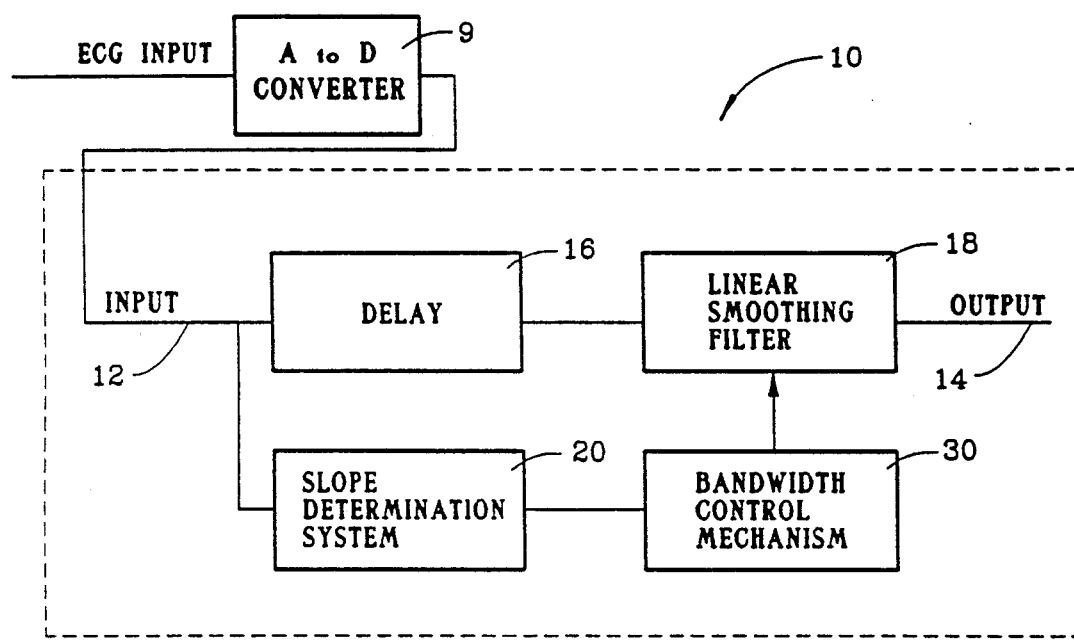
FIG. 1 is a block diagram of the instant invention.

In FIG. 1, the filter system generally labeled 10, is shown in a block diagram of its basic elements. An analog ECG signal taken from each of a series of electrodes placed on a patient is first converted to a digital signal through an A to D converter 9 such as is common in the art. The digitized ECG signals from each electrode are thereafter passed to input 12 of the filter system 10. Input 12 comprises all the ECG leads from the patient. All of the ECG signals are simultaneously passed to delay 16. Selected ECG signals are also simultaneously passed to the slope determination system 20.

Throughout this disclosure reference will be made to parallel processing in various elements of the filter system 10 of either all or selected of the ECG signals. By parallel processing it is meant that a series of input signals produce a corresponding series of output signals. This parallel processing is preferably accomplished by sequential processing by a single digital device such as a microprocessor of the individual input signals during the interval between the collection of samples so that a virtual or apparent parallel processing is performed. Of course, actual parallel processing of the ECG signals could be done by parallel hardware where the input signals are each processed by their own processing hardware. These individual pieces of processing hardware could include individual microprocessors for each signal.

In the preferred embodiment, only the ECG signals from the II, V2 and V5 leads of the commonly applied ECG leads are passed to the slope determination system 20 while each and every ECG lead from the patient's chest is passed to delay 16. A typical input ECG signal is shown in FIG. 3 labeled as "I". In FIG. 3, the horizontal axis represents time and the various electrical signals displayed are aligned vertically so that simultaneous events occur on the same vertical line. It is recognized that the ECG signal shown is representative of the ECG signals detected by each ECG electrode which signals may vary from ECG lead to ECG lead. However, for the purpose of illustrating the operation of the instant invention, only one ECG signal is shown. The inputs for the entire group of ECG leads are labeled in FIG. 2 as 12A-N, where N represents the total number of ECG leads attached to the patient.

The II, V2 and V5 ECG leads are referred to as "basis leads" and are numbered 22A, 22B and 22C respectively. Basis leads II, V2 and V5 are used in slope determination system 20 because of their approximate location on orthogonal axes to each other on the human body. Of course, it is clear that basis leads 22A, B, C correspond to their respective ECG input leads 12 so that the ECG signals from these ECG leads are passed to both the delay 16 and the slope determination system 20. The designation of ECG leads II, V2 and V5 as "basis leads" is for the purpose of clarifying their role in the R wave detection.

Figure 4:
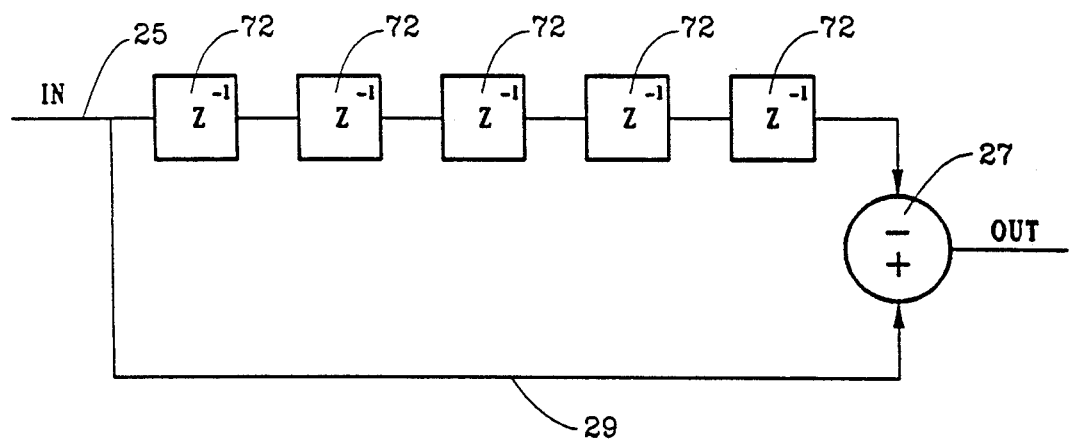
FIG. 4 is a schematic representation of the difference system of the instant invention.
Figure 2:
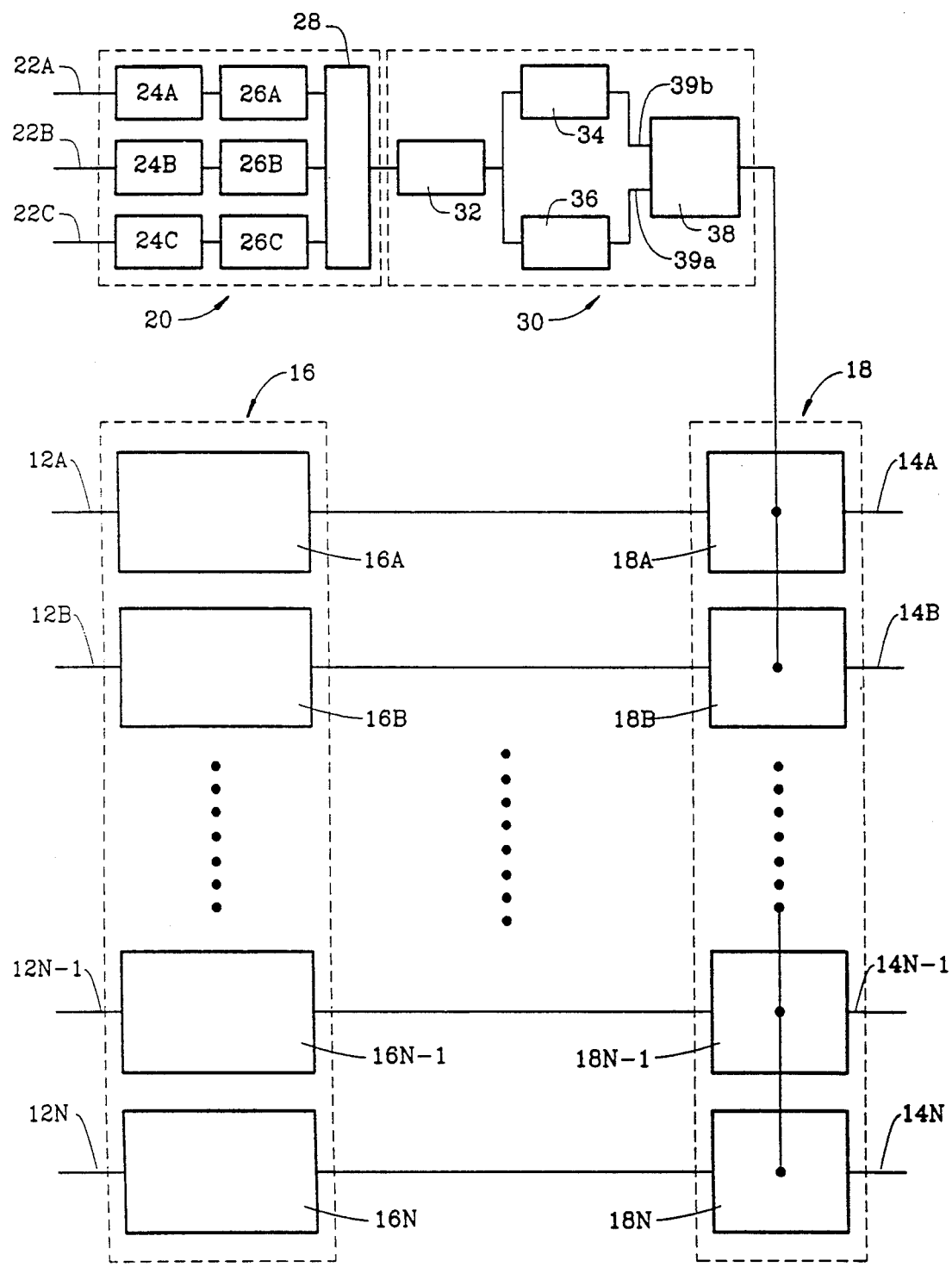
FIG. 2 is a more detailed block diagram of the elements of the block diagram of FIG. 1.
Figure 3:
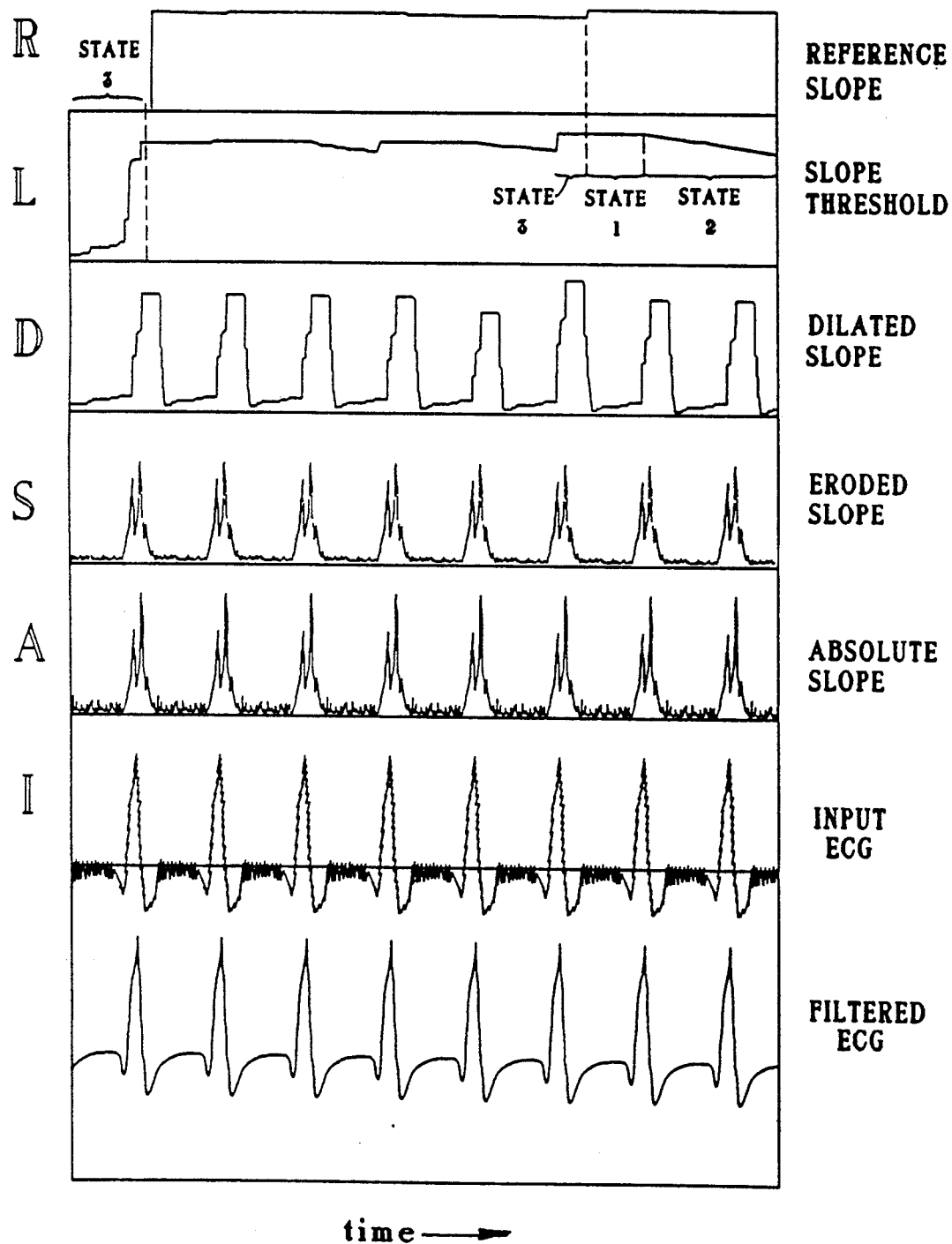
FIG. 3 is a graphic representation of the ECG signal in various stages of processing by the instant invention.

In FIG. 2, the details of slope determination system 20 is contained within the block with the dotted outline labeled 20. Each of the basis leads 22A, 22B, and C is connected to a respective difference system 24A, B, and C. The difference system 24 is a software system shown in block diagram in FIG. 4 which implements the following transfer function:

$$transfer\ function = 1 - Z^{-D}$$

where "D" is the difference parameter. "D" stands for the number of the previous sample whose value is to be subtracted from the value of the current sample. In the preferred embodiment, "D" equals 5 so that the value of the sample 5 previous to the current sample is subtracted from the value of the current sample.

Difference system 24 comprises a series of unit delays 72 connected in serial to an input 25. The unit delays 72 delay the signal for a preselected time. The digital signal from the basis leads 22 is presented to input 25 where it passes from unit delay 72 to unit delay 72 after a pause at each delay corresponding to one sample interval. The digital signal from basis leads 22 presented at input 25 is also simultaneously presented to adder/substracter 27 via line 29. Adder/substracter 27 substracts the value of the input signal delayed by the series of unit delays 72 from the value of the current sample present at input 25.

The purpose of difference system 20 is to get a kind of long term average slope of the input ECG signal. The comparatively long term slope is used because the filter 10 responds to the detection of the R wave to control the filtering process, which R wave has the highest amplitude and also the highest slope over several samples of any part of the ECG signal. The reason the sample point 5 samples prior to the current sample point is used to determine the average slope of the input signal rather than the immediately prior sample point or sample points less than five from the current sample point is that random fluctuations from sample point to sample point or across sample intervals caused by noise including muscle artifact signals may cause measured slopes on these shorter sample intervals to be comparable to the slope of the R wave over the same shorter sample intervals.

This is particularly true where, as is common for such devices, the sample rate for the ECG signal is high, typically on the order of 500 samples per second. However, the muscle artifact signals tend to be random in nature so that the occasionally measured high slopes due to noise or muscle artifact signals are also random and not sustained over several sampling intervals. By contrast, in the case of an R wave, there is a relatively high slope over several sample points upon the sampling of the R wave. Therefore, in order to detect and distinguish the R wave from noise such as muscle artifact noise, a high slope must be maintained over several sample point intervals to indicate the detection of the R wave. For this reason, the difference system determines the slope over 5 sample points so that the local variations due to such things as noise and muscle artifact signals may be effectively averaged out. Because the sample rate in the preferred embodiment is 500 samples per second, the average slope over 5 samples is the average slope over the last 1/100th of a second. The ultimate effect of this difference system 24 is that the R wave clearly stands out from the noise.

The output from the difference system 24A, B, C is passed in parallel to an absolute value system 26. Absolute value system 26 contains individual absolute value systems 6A, B, C, connected to difference system 24A, B, C respectively. Absolute value system 26 finds the absolute value of each slope found by the difference system 24 and passes this absolute value to its output. The slope determination system 20 is interested in determining the absolute slope of the ECG signal since the slope of the R wave will typically have a large positive value as the amplitude of the R wave increases and a large negative value as the amplitide of the R wave decreases. By using the absolute value of the slope, if for some reason the large positive slope of the increase in the amplitude of the R wave is masked or distorted, the system would still be able to detect the R wave from the large absolute value of the slope of the R wave as the amplitude of the R wave decreases. After the absolute values of the slopes determined by the difference systems 24 have been found by the absolute value systems 26, the corresponding outputs of the absolute value systems 26A, B, and C are passed in parallel to the maximum slope determination system 28. Although the absolute value system 26 is used in the preferred embodiment, in an alternate embodiment it may be eliminated so that the output of the difference system 24 is passed directly to the maximum slope determination system 28. In this embodiment, the large negative slope of the R wave as its amplitude decreases would not be used to detect the R wave if the slope of the R wave as its amplitude increases is masked or distorted.

The maximum slope determination system 28 compares the values of the outputs of each absolute value system 26A, B and C and passes the maximum value to its output. The output of maximum slope determination system 28 is shown in FIG. 3 as "A". Because the basis leads II, V2 and V5 are placed in various positions on the body, they each detect the ECG signal in different ways. For this reason, one of the basis leads 22 may detect a higher amplitude of the R wave, which will most likely result in a correspondingly greater slope than that found from the detection of the R wave from other leads. In order to maximize the ability of the instant invention to detect the R wave in a possibly noisy signal contaminated by, among other things, muscle artifact signals, the maximum slope determined by each of the difference systems 24 is used to detect the R wave and consequently control the band width control mechanism 30.

The slope determination system 20 described above uses three basis leads in its determination of the maximum value of the slope of the R wave. However, a greater or lesser number of basis leads could be used where each basis lead would be provided with its own difference system 24 and absolute value determination system 26 whose output would then be passed to maximum slope determination system 28. In fact, a single basis lead having its corresponding difference system 24 and absolute value determination system 26 could be used if desired.

The output of the maximum slope determination system 28 is passed from the slope determination system 20 to the band width control mechanism 30. As shown in FIG. 2, an erode system 32 is located at the input to the band width control mechanism 30. The purpose of the erode system 32 is to minimize the high frequency noise between QRS complexes present on the output of the maximum slope determination system 28. This high frequency noise is manifest as "fuzz" on the ECG signal at the output of the maximum slope determination system 28 which output signal is shown in FIG. 3 labeled "A".

The particular erosion system 32 used in the instant invention is a special case of grayscale erosion defined as:

$$[f \ominus g](n) = min\{f(m) - g(m-n)\}$$

where
$f(k)$ = the signal to be eroded
$g(j)$ = the structuring function
$\ominus$ = the erosion operator
and where
$m \in F$ and $m - n \in G$,
$F$ = the domain of f, and
$G$ = the domain of g.
The structuring function $g(j)$ is defined as:

$$g(j) = \{(0:0 \geq j > -W_{erode}\}$$

i.e. $G = \{0, -1, \ldots, -(W_{erode} - 1)\}$ where $W_{erode}$ is the number of sample points used in the erosion operation. In the preferred embodiment, $W_{erode}$ equals 4, so that the values of "j" are 0, 1, 2 and 3.

In this case, the grayscale erosion is a special case of the well known erosion operation where the value of the structuring function $g(j)$ equals 0 wherever $g(j)$ is defined. Simply put, the erode system 32 in the preferred embodiment, takes the last four samples and finds the minimum value. The minimum value is then passed to the output of the erode system 32. The output of the erosion system 32 is shown in FIG. 3 and is labeled "S". As can been by comparison to the maximum absolute slope "A", also shown in FIG. 3, the eroded slope signal "S" has slightly lower amplitudes on the QRS signal, but has a significant reduction of noise between the QRS complexes. Although in the preferred embodiment the structuring function $g(j)$ equals 0 wherever $g(j)$ is defined, other values of the structuring function may be used as desired.

An excellent discussion of grayscale erosion is found in Chapter 6 of *Non-linear Digital Filter; Principles and Applications* by I. Pitas and A. N. Venetsanopulos, published by Kluwer Academic Publishers, copyright 1990, the teaching of which is incorporated herein by reference.

The output of the erosion system 32 is simultaneously passed to a dilation system 34 and a reference slope determination system 36.

The dilation system 34 used in the instant invention is a special case of grayscale dilation defined as:

$$[f \ominus g](n) = max\{f(m) + g(m-n)\}$$

where
$f(k)$ = the signal to be dilated
$g(j)$ = the structuring function
$\ominus$ = the dilation operator
and where
$m \in F$ and $m - n \in G$,
$F$ = the domain of F, and
$G$ = the domain of g.
The structuring function $g(j)$ is defined as:

$$g(j) = \{(0:0 \geq j > -W_{dilate}\}$$

i.e. $G = \{0, -1, \ldots, -(W_{dilate} - 1)\}$.

where $W_{dilate}$ is the number of sample points used in the dilation operation. In the preferred embodiment, $W_{dilate}$ equals 4, so that the values of "j" are 0, 1, 2 and 3.

In this case, the grayscale dilation is a special case of the well known dilation operation where the value of the structuring function $g(j)$ equals zero wherever $g(j)$ is defined. Although the structuring function $g(j)$ in the preferred embodiment equals 0 wherever $g(j)$ is defined, other values of the structuring function may be used as desired.

The dilation system 34 passes to its output the maximum value for the last predetermined number of samples, called a "dilation sample length", from the erosion system 32. In the preferred embodiment, the dilation sample length equals 47 samples so that the output of dilation system 34 equals the maximum value contained in the last 47 samples. The number 47 is chosen because at a sample rate of 500 samples per second, 47/500 of a second is slightly larger than the time length of a QRS complex. The output of dilation system 34 will eventually be used to time the duration that the linear smoothing filter 18 operates at its highest low pass cut-off frequency in order to pass the QRS wave with a minimum of amplitude reduction. The output of dilation system 34 is passed to a ratio determination system 38 at ratio input 39(b). The output signal of dilation system 34 is shown in FIG. 3 labeled as "D".

An excellent discussion of grayscale dilation is found in Chapter 6 of *Non-linear Digital Filter; Principles and Applications* by I. Pitas and A. N. Venetsanopulos, published by Kluwer Academic Publishers, copyright 1990, the teaching of which is incorporated herein by reference.

As stated, the output from the erosion system 32 is passed to a reference slope determination system 36 simultaneously as the output from the erosion system 32 is passed to the dilation system 34. The reference slope determination system 36 holds the long term maximum slope found by the maximum slope determination system 28 and passed through the erosion system 32 as directed by a software controlled state machine shown symbolically in FIG. 5. The state machine is used to find the new peak on the reference slope shown in FIG. 3, labeled as "R". A slope threshold, shown in FIG. 3 labeled as "L", is used as a long term maximum value of the eroded slope "S" which may decay in time if the values of "S" fail to periodically have comparatively high values. The state machine compares the values of the eroded slope "S" to the slope threshold "L" to determine the reference slope "R".

The state machine consists of states "0", "1", "2", and "3" which represent logical conditions. The logical conditions are dependent upon the relative values of "L", "S", and "R" as well as the values stored in counters used with the state machine. When the relationships or values of these registers and counters changes, the state machine moves from whatever state it is in to a different state as will be described hereafter.

Figure 5:
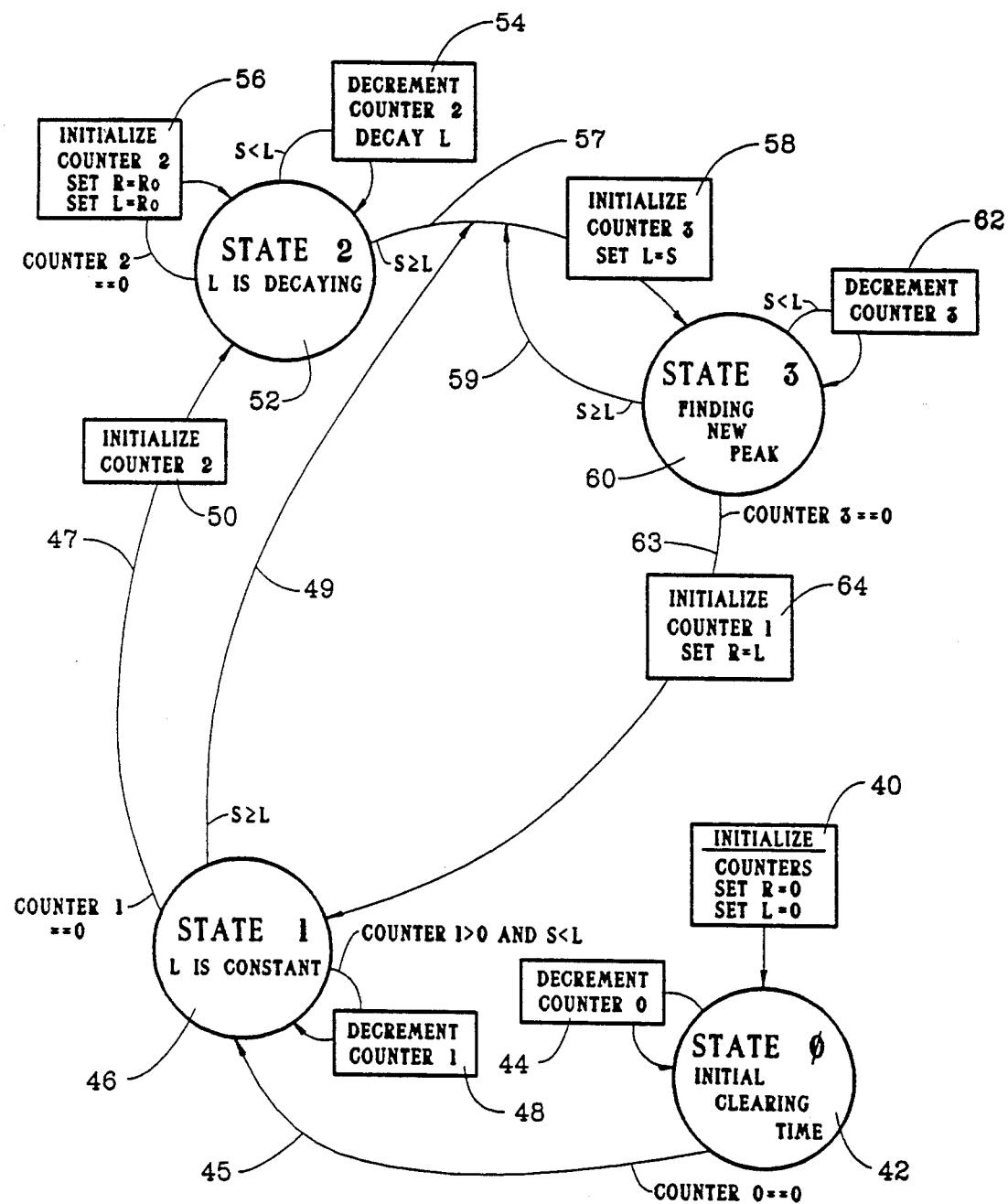
FIG. 5 is a state diagram showing the implementation of the reference slope detection system.

The state machine of FIG. 5 uses "Counters 0-3" which correspond to "States 0-3". Counter 0 is used to time an initial pause while the state machine accumulates a reservoir of samples for the state machine to work with. Counter 1 is used as the timer for "State 1", the logical state where the slope threshold "L" is a constant. Counter 2 is used as a timer for logical "State 2" which causes the slope of threshold "L" to decay while no new peak value of the eroded slope "S" is found. Counter 3 is used as the timer for logical "State 3" which finds a new peak for slope threshold "L" when the eroded slope "S" is greater than or equal to the slope threshold "L".

A special symbol, "==", is used in FIG. 5 between a reference to one of the Counters 0-3 on its left side and the number 0 on its right side such as "Counter 1 ==0". This symbol, "==", means that when the respective Counter contains the value "0", the program leaves the logical state corresponding to that counter along the path adjacent to the phrase containing the "==" symbol.

The machine begins at step 40 which initializes Counter 0 to 75 and Counter 1 to 160. In addition, the value of the register R, which contains the reference slope "R", and the value of register L, which contains the slope threshold "L", are both set equal to 0. After Counters 0 and 1 have been initialized and registers R and L set equal to 0, the program passes from step 40 to "State 0" which is labeled 42. "State 0" 42 is the Initial Clearing Time state for the state machine. While at "State 0", the program passes in a loop from "State 0" 42 back to "State 0 42 through step 44 which decrements Counter 0 from its initial value of 75 to 0. During this time, transient effects from turning on the device are allowed to dissipate and a collection of sample points is accumulated. When Counter 0 has decremented to 0, the program leaves "State 0" 42 and passes to "State 1" labeled 46 along path 45.

"State 1" is a logical state where the program will reside while the value of the slope threshold "L" is held constant. As noted above, in the initialization step 40, the value of the slope threshold "L" is set equal to zero. At "State 1", the value of the eroded slope "S" is constantly compared to the value of the slope threshold "L". These relative values must either be such that the value of "S" is less than, equal to, or greater than the value of "L". Accordingly, in "State 1" as well as in "State 2" and "State 3", the relationship between "S" and "L" determines the path from the respective "States 1, 2 and 3". The only exception to this general rule is where a counter associated with "States 1, 2 or 3" has been allowed to decrement to zero. When this occurs, regardless of the relationship between "S" and "L", the program must exit that "State" along the path indicating that the counter has decremented to zero.

Initially, as the program passes from "State 0" 42 to "State 1" 46, the value of the eroded slope "S" will be equal to or greater than the initial value of threshold slope "L" which has been initialized to zero. Therefore, the program will pass from "State 1" along path 49 to step 58. Step 58 initializes Counter 3 to 75 and sets the value of the slope threshold "L" equal to the value of the eroded slope "S". In other words, the value of the slope threshold "L" is now set equal to the higher or equal value of the eroded slope "S".

From step 58, the program passes to "State 3" labeled 60. The purpose of "State 3" 60 is to find a new peak for the reference slope "R". While at "State 3" 60, so long as the value of the eroded slope "S" is greater than or equal to the value of the threshold slope "L", the program will loop from "State 3" 60 through step 58 back to "State 3" 60. This has the effect of raising the value of "L" to the continuously increasing value of "S". However, if the value of "S" becomes less than the value of "L", the program will pass from "State 3" 60 through step 62, which decrements Counter 3 by 1, back to "State 3" 60.

So long as "S" remains less than "L", and the value of Counter 3 is greater than zero, the program will loop from "State 3" 60 through step 62 back to "State 3" 60 while decrementing Counter 3. If, however, the value of "S" becomes greater than or equal to "L", the program will immediately exit "State 3" 60 and loop through step 58 back to "State 3" 60 thereby raising "L" to the new higher value of "S" and re-initializing Counter 3. If, however, no value of "S" is greater than or equal to "L" while Counter 3 decrements, when Counter 3 reaches 0, the program passes from "State 3" 60 along path 63 to step 64. Step 64 initializes Counter 1, in the preferred embodiment, to 160, and sets the value of the reference slope "R" equal to the value of the slope threshold "L". Leaving "State 3" 60 by path 63 indicates that a new peak for the reference slope "R" has been found. Thereafter, the program continues along path 63 from step 64 to "State 1" 46, where the value of the slope threshold "L" will be continuously compared to the value of the eroded slope "S".

The program will stay at "State 1" 46 and the value of the slope threshold "L" will be held constant while the value of the eroded slope "S" is less than the value of the slope threshold "L" and Counter 1 has a value greater than 0. When both of these conditions occur, the program loops from "State 1" back to "State 1" through step 48 which decrements Counter 1 from its initial value of 160. However, if the value of "S" becomes equal to or greater than the value of "L", the program exits "State 1" 46 through path 49 to step 58 as explained above.

If Counter 1 is allowed to decrement to 0, "State 1" is exited through path 47 marked "Counter 1==0" where the program passes to step 50. Step 50 initializes Counter 2 to 1000. Thereafter, the program continues on path 47 to "State 2" labeled 52, which is the state where the value of the slope threshold "L" is decayed. In "State 2", if the value of the eroded slope "S" is less than the value of the slope threshold "L" the program passes through step 54. Step 54 decrements Counter 2 by 1 and multiplies the current value of the slope threshold "L" by a decay value. In the preferred embodiment, the decay value equals 0.9995. So long as the value of "S" is less than "L" the value of "L" will decay by 0.05% on each pass through step 54 until the value of Counter 2 is decremented to 0. Because Counter 2 was initialized to contain 1000 and because "L" decays by 0.05% on each loop through step 54, after passing through step 54 for the 1000 counts in Counter 2, the value of "L" will decay to 0.606 its original value. This process of having "L" decay is shown in FIG. 3 labeled "State 2" on the signal line corresponding to the threshold slope "L".

When the value of Counter 2 has decremented to 0, as indicated by the label "Counter 2==0", the program passes to step 56. Step 56 initializes Counter 2 to a new value of 1000, and sets "R", the reference slope value, and the slope threshold "L" equal to $R_0$. $R_0$ is chosen to represent a small, possibly even zero value. A non-zero value for $R_0$ may be chosen so that the program will remain at "State 2" 52 for small values of the eroded slope. If a zero value is chosen for $R_0$, the program will immediately leave "State 2" 52 via path 57 to step 58 because the value for "S" will be greater than or equal to the zero value for "L". From step 56, the program continues back to "State 2" 52. If "S" remains less than "L", the program will continue to pass through step 54, looping from "State 2" back to "State 2" as described above. In this way, the value of the slope threshold "L" will continue to decay.

However, if the value of the eroded slope "S" becomes greater than or equal to the value of the slope threshold "L", the program exits "State 2" 52 along path 57 and passes to step 58 where the process of finding a new peak value for the reference slope "R" is determined as described above.

The value of "160" is used to initialize Counter 1 so that "L" will remain constant for a time of 160/500 of a second before the value of "L" is decayed by passing to "State 2" 52. This allows the state machine to avoid moving to "State 3" 60 upon detection of a value for "S" larger than the decayed value of "L". Therefore, if the state machine moved from "State 1" 46 to "State 2" 52 immediately upon "S" becoming less than "L", the value of "L" would immediately begin to decay by the program passing through step 54. Since "L" is decaying, a value of "S" greater than or equal to the decayed value of "L" will cause the program to exit "State 2" 52 along path 57 and pass to "State 3" 60 through step 58. Once in "State 3" 60, the program will exit "State 3" 60 through step 64 which will set the value of the reference slope "R" to the value of "L" which was set in step 58 to the comparatively lower value of "S". This value of the eroded slope "S" which now has set the value of the reference slope "R" could be lower than value of the eroded slope "S" that would move the program from "State 1" 46 to "State 3" 60 when the program pauses at "State 1" 46 by looping through step 48. By pausing at "State 1" 46, the value of "L" remains higher than the decayed value of "L" found in "State 2" 52 so that a higher value of the eroded slope "S" is required to enter "State 3" 60 which higher value of the eroded slope "S" becomes the new value for the reference slope "R".

As can be seen, step 58 may be entered from either "State 1" along path 49, "State 2" along path 57 or "State 3" along path 59. Regardless of the path taken to step 58, the actions of step 58, and the corresponding passing of the program into and the operation of "State 3", occur independently of the path taken to enter step 58. Further, it is to be noted that paths 49, 57 and 59 all leave their respective states upon the condition that the value of "S" is greater than or equal to the value of "L". This has the effect of allowing a new peak for the reference slope "R" to be found regardless of which state the state machine finds itself in.

The output of the reference slope determination system 36 is the reference slope "R". The reference slope "R" is passed to the ratio system 38 through ratio input 39(a).

Ratio determination system 38 compares the output from the dilation system 34, which is shown in FIG. 3 labeled as the dilated slope "D", with the output of the reference sloped determination system 36 which is shown in FIG. 3 labeled as reference slope "R" to produce a ratio "r".

As can be seen in FIG. 3, the value of the dilated slope "D" increases substantially with the presence of the R wave, and remains high for the "dilation sample length", which in the preferred embodiment is 47 samples. This is because the current dilated slope value is the maximum value of the slopes of the last 47 samples. In the time before the presence of the R wave in the ECG signal, the slope values of the ECG signal are typically comparatively small. However, with the presence of the R wave, the slope of the ECG signal at the R wave becomes quite high so that as the R wave begins its rapid climb in amplitude, a correspondingly high slope is also present. By contrast, the reference slope "R" is the maximum value for the eroded slope found during operation of the state machine unless no R waves are found. If for some reason, no subsequent R waves are detected after an initial R wave is detected, the reference slope "R" is set to a low value $R_0$ by step 56 of "State 2" of the state machine of the reference slope determination system 36. As soon as a subsequent R wave is detected, the state machine will re-establish a maximum value for the reference slope "R" as explained above.

Referring to FIG. 3, after an initial time has elapsed to establish a reference slope "R" having a relatively high value corresponding to the detection of the "R" wave, when the value of reference slope "R" and dilated slope "D" differ substantially, the "dilation sample length" after the detection of the R wave has passed. The resulting dilated slope "D" with a relatively low value corresponds to the portion of the input ECG signal between QRS complexes.

As an R wave is detected, the ratio "r" of "R" to "D" will approach 1. The ratio "r" of reference slope "R" to dilated slope "D" will be near 1 when the dilation slope "D" indicates the presence of an "R" wave and for the "dilation sample length" thereafter. After the R wave passes and the dilation time length has passed, the ratio "r" will decrease toward 0. Ratio determination system 38 produces an output signal indicative of the ratio "r" of the reference slope "R" to the dilated slope "D". The output signal from ratio determination system 38 is passed to linear smoothing filter 18 to determine the cut-off frequency of filter 18.

Figures 6A, 6B:
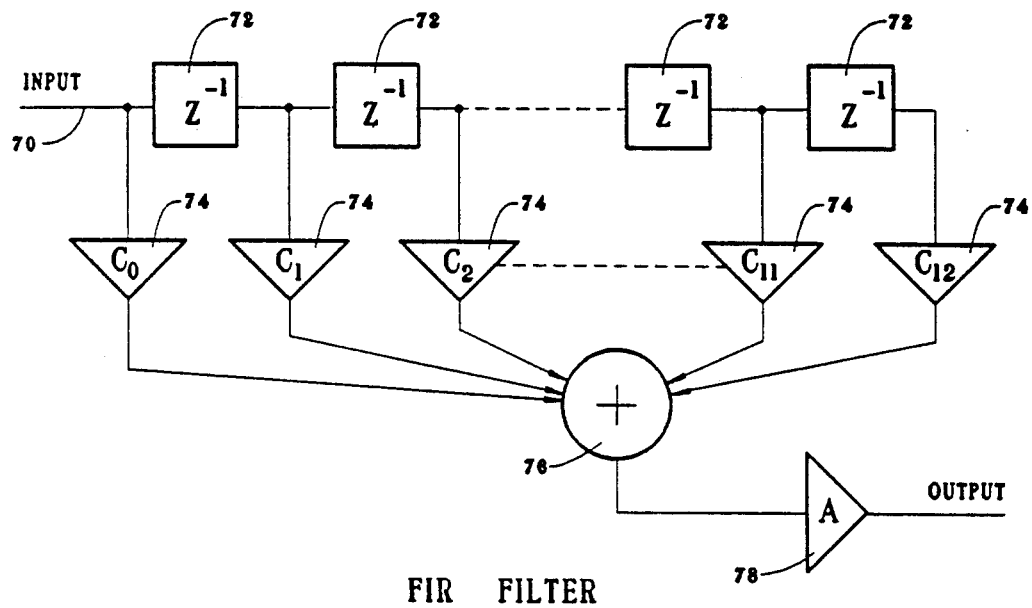
FIG. 6A is a schematic representation of the FIR filter of the instant invention.
FIG. 6B is a chart containing the co-efficient values for the multiplication blocks of the FIR filter of FIG. 6A and the corresponding cut-off frequencies.

Filter 18, is preferably a finite impulse response (FIR) filter as shown schematically in FIG. 6A. Chapter 8 of *Digital Signal Processing*, 42nd Edition, by William D. Stanley, Gary R. Dougherty and Ray Dougherty contains an excellent treatment of digital FIR filters and their design, the teaching of which is incorporated herein by reference.

In the preferred embodiment, the FIR filter is a twelfth order filter. Also in the preferred embodiment, filter 18 has six different cut-off frequencies shown in the chart of FIG. 6B corresponding to different values of ratio "r" so that the filter 18 can smoothly change cut-off frequencies from the lowest to the highest cut-off frequencies, and vice-versa, without abrupt changes in the output of filter 18. Without such transitional filtering, the switch from the minimum to maximum filtering would manifest itself in an abrupt transition in the output ECG signal which would affect the diagnostic value of the ECG.

The cut-off frequency used in filter 18 depends on the ratio "r" of the dilated slope "D" to the reference slope "R" as explained above. Different values of ratio "r" are designated by subscripts from 0 to 5 corresponding to the 6 different cut-off frequencies. As shown in FIG. 6B, when the ratio "r" is greater than or equal to 0.64, corresponding to a ratio of "$r_0$", the filter operates at its maximum cut-off frequency. Conversely, when the ratio "r" is less than 0.2, corresponding to a ratio of "$r_5$", the filter operates at its minimum cut-off frequency. The other four cut-off frequencies correspond to the following values for "r": $0.53 \leq r_1 < 0.64$, $0.42 \leq r_2 < 0.53$, $0.31 \leq r_3 < 0.42$, and $0.2 \leq r_4 < 0.31$.

As stated, the schematic representation of the filter 18 is shown in FIG. 6A. In FIG. 6A, the ECG signal from delays 16A-N are passed to filter input 70. In the preferred embodiment, filter 18 is implemented on a microprocessor. In this case, each ECG signal is preferably passed to filter 18 in a sequential order so that virtual parallel processing of the ECG signals takes place. However, each ECG signal may have its own filter 18 as desired. From filter input 70, the input ECG signal is sequentially passed through a series of unit delays 72. In the preferred embodiment, filter 18 has 12 unit delays 72. A multiplication block 74, denoted as $C_n$ according to the coefficient values it will contain as explained hereafter, is connected to the line before each unit delay 72. In the schematic representation of FIG. 6A, a line connecting unit delays 72 or leading from the line connecting unit delays 72 to multiplication blocks 74 indicates that whatever digital value is present on the line is presented to all points along the line simultaneously. In the preferred embodiment there are 12 unit delays 72 with 12 corresponding multiplication blocks $C_0$ through $C_{11}$ connected to the inputs of the 12 unit delays 72. In addition, the output of the twelfth and farthest unit delay 72 from filter input 70 is connected to a multiplication block $C_{12}$ so that there are a total of 13 multiplication blocks 74.

Multiplication blocks $C_0$ through $C_{12}$ contain corresponding coefficients also denoted as values of $C_0$ through $C_{12}$ which are multiplied by the values of the processed ECG signal presented to the inputs of multiplication blocks $C_0$ through $C_{12}$. The values of the coefficients determines the cut-off frequency of the filter 18 according to the operation of such FIR filters as is well understood in the art. The coefficients $C_0$ through $C_{12}$ for the respective cut-off frequencies are shown in the chart of FIG. 6B. The cut-off frequencies corresponding to the use of respective coefficients $C_0$ through $C_{12}$ are also shown in FIG. 6B.

The resulting values from multiplication blocks 74 are passed to adder 76 which adds the values from each of the multiplication blocks 74 and passes the sum to normalizing block 78. Normalizing block 78 multiplies the output from adder 76 by the inverse of the sum of the values of the coefficients $C_0$ through $C_{12}$. The result of this multiplication operation is passed to the output 14 of the filter 18.

As mentioned, each of the ECG inputs 12A-N are passed to the delay 16 which delays the input ECG signal for an amount of time equal to the processing time of the slope determination system 20 and the band width control mechanism 30 plus one half of the dilation sample length. This timing allows the R wave in the input ECG signal to be precisely centered in time on the "window" that the filter 18 is open to its maximum cut-off frequency as directed by the band width control mechanism 30 as described above. After each ECG input 12A-N is delayed in its respective delay 16A-N, each individual ECG input signal 12A-N is passed to its corresponding FIR filter 18A-N. As mentioned, each of these individual ECG signals is preferably sequentially passed to a single digital FIR filter 18 so that a series of virtual parallel filters 18A-N is produced. After each ECG input signal 12A-N has been filtered in filter 18, the filtered ECG signal is output through output 14A-N of filter 18 to an appropriate device to record or display the respective filtered ECG signals such as a video display screen or a chart recorder.

The source code implementing the instant invention, including the state machine shown in FIG. 5 and described above, is in the attached Appendix I.

The instant invention has been described in connection with a specific embodiment. However, the details described herein in connection with the disclosure of the embodiment have been given by means of example and not for limitation. It is clear that changes and modifications may be made to the description contained herein and still be within the scope of the invention. Further, obvious changes and modifications will occur to those skilled in the art.

APPENDIX I

```
*************************************************************

Written by Victor M. dePinto
© 1991 QUINTON INSTRUMENT CO. All rights reserved.

************************************************************* include <math.h>
include <stdlib.h>
#include <psdef.h>

/* Unit delays for the analysis lowpass filters */
static double analysis_LPF_unit_delay[NUMBER_OF_ECG_CHANNELS][3];

/* Unit delays for the display variable bandwidth lowpass filters */
static double
    display_LPF_unit_delay [NUMBER_OF_ECG_CHANNELS][MUSCLE_FILTER_LENGTH];

/* Unit delays for the delays ahead of the display FIR filters */
static double
    display_delay_unit_delay [NUMBER_OF_ECG_CHANNELS][PREFILTER_DELAY_LENGTH];

/* Unit delays for the 3 basis lead differences */
static double difsamples0[DIFFERENCE_ORDER],
              difsamples1[DIFFERENCE_ORDER],
              difsamples2[DIFFERENCE_ORDER];

static int State;              /* State of Reference Slope state machine */
static int ctr1, ctr2, ctr3, ctr4;   /* Counters used by the state machine */
static double reference_slope;       /* Variables used by the state machine */
static double slope_threshold;

static double max_absolute_slope3, eroded_slope, dilated_slope;
static enum filter_bandwidth FIR_bandwidth; /* Bandwidth of display FIR filter */
static double dilate_delays[DILATION_SIZE],  /* Data history of dilation  */
       erode_delays[EROSION_SIZE];           /* Data history of erosion   */
static int dilate_ndx, erode_ndx;

/*-----------------------------------------------------------
*/
int
init_muscle_artifact_filter()
{
int channel, k;

reference_slope = slope_threshold = 0.0;
State = INITIAL_CLEARING;
ctr1 = CTR1_PERIOD;
ctr2 = CTR2_PERIOD;
ctr3 = CTR3_PERIOD;
ctr4 = CTR4_PERIOD;
dilate_ndx = erode_ndx = 0;
```

```c
/* Init analysis LPF unit delays. */
for (channel = 0; channel < NUMBER_OF_ECG_CHANNELS; ++channel)
    for (k = 0; k < 3; ++k)
        analysis_LPF_unit_delay [channel][k] = 0.0;

/* Init display prefilter delay unit delays. */
for (channel = 0; channel < NUMBER_OF_ECG_CHANNELS; ++channel)
    for (k = 0; k < PREFILTER_DELAY_LENGTH; ++k)
        display_delay_unit_delay [channel][k] = 0.0;

/* Init display LPF unit delays. */
for (channel = 0; channel < NUMBER_OF_ECG_CHANNELS; ++channel)
    for (k = 0; k < MUSCLE_FILTER_LENGTH; ++k)
        display_LPF_unit_delay [channel][k] = 0.0;

/* Init erosion unit delays. */
for (k = 0; k < EROSION_SIZE; ++k)
    erode_delays[k] = 0.0;

/* Init dilation unit delays. */
for (k = 0; k < DILATION_SIZE; ++k)
    dilate_delays[k] = 0.0;

/* Init difference unit delays. */
for (k = 0; k < DIFFERENCE_ORDER; ++k) {
    difsamples0[k] = 0.0;
    difsamples1[k] = 0.0;
    difsamples2[k] = 0.0;
}
}

/*-------------------------------------------------------------
    Determine the bandwidth of the FIR lowpass filter for the
    display channels. The bandwidth is controlled by the slope
    of the ECG signal; When slope is greatest, as during the QRS
    complex, the bandwidth is maximum. When slope is low, the
    bandwidth is reduced in order to attenuate low amplitude noise.

First, the maximum of the absolute values of the slopes of
    3 ECG channels is found. This maximum absolute slope is passed
    through an erosion operator and then a dilation operator.
    the resulting dilated slope is compared with a reference slope
    in order to determine the instantaneous bandwidth of the FIR
    lowpass filter.

The reference slope mentioned above is essentially the
    long-term maximum of the absolute slope.

This function returns the instantaneous bandwidth of the
    display lowpass filter.
*/
enum FIR_filter_bandwidth
bandwidth_control(basis_x, basis_y, basis_z,
            difference_order, erosion_size, dilation_size)
    double basis_x,   /* The three basis leads whose slope is used */
           basis_y,   /* to control the bandwidth of the muscle    */
```

```
            basis_z;     /* artifact filter                    */
      int difference_order;  /* Order of the difference */
      int erosion_size;      /* Size of the erosion     */
      int dilation_size;     /* Size of the dilation    */
{
int j;
double abslope0, abslope1, abslope2;
double filter_out, sum, output_multiplier;

/* Find max absolute slope of three basis leads */
abslope0 = fabs(difference(basis_x, difsamples0, difference_order));
abslope1 = fabs(difference(basis_y, difsamples1, difference_order));
abslope2 = fabs(difference(basis_z, difsamples2, difference_order));
max_absolute_slope3 = max(abslope2, (max(abslope0, abslope1)) );

/* Erode max absolute slope of the 3 basis leads */
eroded_slope = erode__(max_absolute_slope3, erode_delays, erosion_size);
/* Dilate the eroded slope */
dilated_slope = dilate__(eroded_slope, dilate_delays, dilation_size);
/* Adjust the reference slope value */
determine_reference_slope(eroded_slope);

/* Determine the bandwidth of the display FIR lowpass filter as a
   function of the ratio of dilated_slope to reference_slope.
*/
if (dilated_slope < .2 * reference_slope)
   FIR_bandwidth = BANDWIDTH_17_HZ;
else
   if (dilated_slope < .31 * reference_slope)
      FIR_bandwidth = BANDWIDTH_25_HZ;
   else
      if (dilated_slope < .42 * reference_slope)
         FIR_bandwidth = BANDWIDTH_32_HZ;
      else
         if (dilated_slope < .53 * reference_slope)
            FIR_bandwidth = BANDWIDTH_45_HZ;
         else
            if (dilated_slope < .64 * reference_slope)
               FIR_bandwidth = BANDWIDTH_77_HZ;
            else
               FIR_bandwidth = BANDWIDTH_100_HZ;

return (FIR_bandwidth);   /* Return bandwidth */
} /* End bandwidth_control() */

/*----------------------------------------------------------------
   Delay the ECG signal by a certain number of samples.
   This delay function is used ahead of the display FIR filters.
*/
double
display_prefilter_delay(input_sample, channel)
      double input_sample;  /* The present input sample value  */
      int channel;          /* Channel number                  */
{
double output_sample;
int j;
```

```
output_sample = display_delay_unit_delay[channel][PREFILTER_DELAY_LENGTH - 1];
for (j = PREFILTER_DELAY_LENGTH - 1; j > 0; --j)    /* Shift in new sample */
    display_delay_unit_delay[channel][j] =
        display_delay_unit_delay[channel][j - 1];
display_delay_unit_delay[channel][0] = input_sample;
return (output_sample);
} /* End display_prefilter_delay() */

/*---------------------------------------------------------------
    FIR lowpass filter used in the display channels.
    The cutoff frequency of this filter can be varied from 17 Hz
    to 100 Hz. If the muscle artifact filter is switched on,
    the filter will normally operate at 100 Hz bandwidth during
    the QRS complex and at lower bandwidth during other parts
    of the ECG wave in order to reduce low amplitude noise.
*/
double
display_FIR_filter(new_sample, bandwidth, channel)
    double new_sample;                  /* The present input sample value */
    enum FIR_filter_bandwidth bandwidth; /* Desired bandwidth              */
    int channel;                        /* Channel number                 */
{
int j;
double sum, filter_out, output_multiplier;

for (j = MUSCLE_FILTER_LENGTH - 1; j > 0; --j)       /* Shift in new sample */
    display_LPF_unit_delay[channel][j] = display_LPF_unit_delay[channel][j-1];
display_LPF_unit_delay[channel][0] = new_sample;

/* Form the sum of a number of points which depends on the desired bandwidth */
sum = 0.0;
switch (bandwidth) {
    case BANDWIDTH_100_HZ:
        sum = display_LPF_unit_delay[channel][6];       /* Length = 3 */
        sum += 0.367 * display_LPF_unit_delay[channel][5]; /* Zone r0   */
        sum += 0.367 * display_LPF_unit_delay[channel][7];
        output_multiplier = 0.576701268743; /* 1 / (1 + 2 * 0.367) */
        break;
    case BANDWIDTH_77_HZ:               /* Length = 3 */
        for (j = 5; j <= 7; ++j)         /* Zone r1   */
            sum += display_LPF_unit_delay[channel][j];
        output_multiplier = 0.333333333333; /* 1/3 */
        break;
    case BANDWIDTH_45_HZ:               /* Length = 5 */
        for (j = 4; j <= 8; ++j)         /* Zone r2   */
            sum += display_LPF_unit_delay[channel][j];
        output_multiplier = 0.2;  /* 1/5 */
        break;
    case BANDWIDTH_32_HZ:               /* Length = 7 */
        for (j = 3; j <= 9; ++j)         /* Zone r3   */
            sum += display_LPF_unit_delay[channel][j];
        output_multiplier = 0.142857142857; /* 1/7 */
        break;
    case BANDWIDTH_25_HZ:               /* Length = 9 */
        for (j = 2; j <= 10; ++j)        /* Zone r4   */
            sum += display_LPF_unit_delay[channel][j];
```

```
            output_multiplier = 0.111111111111;  /* 1/9 */
            break;
    case BANDWIDTH_17_HZ:                  /* Length = 13 */
            for (j = 0; j <= 12; ++j)      /* Zone r5    */
                sum += display_LPF_unit_delay[channel][j];
            output_multiplier = 0.0769230769231; /* 1/13 */
            break;
    default:
            printf("FIR filter bandwidth error.\n");
}
filter_out = sum * output_multiplier; /* Multiply sum by output gain. */
return (filter_out);
} /* End FIR_filter */

/*-----------------------------------------------------------
    100 Hz lowpass filter for analysis channels.
    This is a second order (3 tap) FIR filter.
*/
double
analysis_FIR_filter(new_sample, channel)
    double new_sample;  /* The present input sample value */
    int channel;        /* Channel number                 */
{
int j;
double sum, filter_out, output_multiplier;

for (j = 2; j > 0; --j)    /* Execute the delay */
    analysis_LPF_unit_delay[channel][j] = analysis_LPF_unit_delay[channel][j-1];
analysis_LPF_unit_delay[channel][0] = new_sample;   /* Shift in new sample */ sum = 0.367 * analysis_LPF_unit_delay[channel][0];
sum += analysis_LPF_unit_delay[channel][1];
sum += 0.367 * analysis_LPF_unit_delay[channel][2];
output_multiplier = 0.576701268743;   /* 1 / (1 + 2 * 0.367)  */
filter_out = sum * output_multiplier; /* Multiply sum by output gain. */
return (filter_out);
} /* End analysis_LPF */

/*-----------------------------------------------------------
    Find the minimum value of the latest N samples, and store
    the latest sample in a history array.
*/
double
erode__ (new_sample, past_samples, size)
    double new_sample;       /* The present sample value */
    double past_samples[];   /* Storage for past samples */
    int size;                /* N in the above description */
{
double min_val;
int j;

past_samples[erode_ndx++] = new_sample;   /* Put new value in array */
if (erode_ndx >= size)          /* Bump array index */
    erode_ndx = 0;
min_val = 1.0e300;                        /* Find min */
for (j = 0; j < size; ++j)
```

```
      if (past_samples[j] < min_val)
            min_val = past_samples[j];
return(min_val);
} /* End erode__ */

/*--------------------------------------------------------------
      Find the maximum value of the latest N samples, and store
      the latest sample in a history array.
*/
double
dilate__(new_sample, past_samples, size)
      double new_sample;      /* The present sample value   */
      double past_samples[];  /* Storage for past samples   */
      int size;               /* N in the above description */
{
double max_val;
int j;

past_samples[dilate_ndx++] = new_sample;     /* Put new value in array */
if (dilate_ndx >= size)   /* Bump array index */
      dilate_ndx = 0;
max_val = 0.0;                               /* Find max */
for (j = 0; j < size; ++j)
      if (past_samples[j] > max_val)
            max_val = past_samples[j];
return(max_val);
} /* End dilate__ */

/*--------------------------------------------------------------
      Determine the reference slope, which is compared with dilated
      slope in order to determine the display LPF bandwidth.

The reference slope is essentially a long term maximum of the
      absolute value of the slope of the ECG signal. An exponentially
      decaying quantity called the slope threshold is compared with
      the parameter __slope. If __slope is greater than slope_threshold,
      slope_threshold is set equal to __slope and a counter is started.
      when the counter times out, the short term maximum slope has
      been found, and reference_slope is set equal to slope_threshold.
      Note that reference_slope is modified only if __slope exceeds
      slope_threshold, and is a long-term maximum absolute slope.

This function is a state machine.

*/
determine_reference_slope(__slope)
      double __slope;
{ switch (State) {
   case INITIAL_CLEARING:
         if (--ctr4 <= 0)
               State = SLOPE_THRESHOLD_CONSTANT;
         break;
   case SLOPE_THRESHOLD_CONSTANT:
         if (__slope >= slope_threshold) {
```

```
            State = FINDING_NEW_PEAK;
            ctr2 = CTR2_PERIOD;
            slope_threshold = _slope;
            break;
        }
        if (--ctr1 <= 0) {
            State = SLOPE_THRESHOLD_DECAYING;
            ctr3 = CTR3_PERIOD;
            break;
        }
        break;
    case SLOPE_THRESHOLD_DECAYING:
        if (_slope >= slope_threshold) {
            State = FINDING_NEW_PEAK;
            ctr2 = CTR2_PERIOD;
            slope_threshold = _slope;
        }
        else {
            slope_threshold *= 0.9995;
            if (--ctr3 <= 0) {
                ctr3 = CTR3_PERIOD;
                slope_threshold = 100.0;
                reference_slope = 100.0;
            }
        }
        break;
    case FINDING_NEW_PEAK:
        if (_slope >= slope_threshold) {
            ctr2 = CTR2_PERIOD;
            slope_threshold = _slope;
            break;
        }
        if (--ctr2 <= 0) {
            reference_slope = slope_threshold;    /* New peak found */
            ctr1 = CTR1_PERIOD;
            State = SLOPE_THRESHOLD_CONSTANT;
            break;
        }
        break;
} /* End switch */
} /* End determine_reference_slope */

/*----------------------------------------------------------
    Compute the Nth order difference. (i.e. the value of the
    present sample minus the value N sample intervals previous.)
*/
double
difference(new_sample, past_samples, difference_order)
    double new_sample;         /* The present sample value  */
    double past_samples[];    /* Storage for past samples   */
    int difference_order;     /* N in the above description */
{
int j;
double difference;

/* Compute value of nth order difference */
```

```
difference = new_sample - past_samples[difference_order-1];
for (j = difference_order-1; j > 0; --j)    /* Shift the history array */
    past_samples[j] = past_samples[j-1];    /* Element 0 is most recent */
past_samples[0] = new_sample;               /* Enter new sample in history array */
return(difference);
}

/*-----------------------------------------------------------
```

What is claimed is:

1. A device for filtering unwanted electrical signals from an electrocardiograph (ECG) signal presented to an input comprising:
   a) a variable cutoff frequency low pass filter capable of operating at at least two different cutoff frequencies, each specific cutoff frequency enabled in response to a control signal;
   b) means, connected to the input and said low pass filter, for delaying an ECG signal presented at the input before passing the ECG signal to said low pass filter;
   c) means, connected to the input, for determining the presence of a QRS complex in the ECG signal and for creating a control signal in response thereto, said control signal having a plurality of states, each of said states corresponding to a specific cutoff frequency of said low pass filter, said control signal passed to said low pass filter;
   whereby during the part of the ECG signal presented to the input not having a QRS complex, said means for determining the presence of a QRS complex and creating a control signal creates a control signal in a first state, said control signal in said first state directing said low pass filter to operate at said relatively low cutoff frequency and when a QRS complex is detected in the ECG signal by said means for determining the presence of a QRS complex, said means for determining the presence of a QRS complex and creating a control signal creases a control signal in a second state, said control signal in said second state directing said low pass filter to operate at said relatively higher cutoff frequency so that the QRS complex of the ECG signal delayed by said means for delaying is presented to said low pass filter just after said low pass filter begins operating at said relatively higher cutoff frequency, thereby passing the QRS complex through said low pass filter with relatively little attenuation.

2. The device of claim 1 wherein said means for determining the presence of a QRS complex includes a means for determining the instantaneous slope of the ECG signal.

3. The device of claim 1 wherein said means for delaying an ECG signal includes an electronic memory for storing the ECG signal presented to the input for later recall.

4. The device of claim 1 wherein said control signal created by said means for determining the presence of a QRS complex is maintained, in response to a determination that a QRS complex is present, for a time approximately equal to the time duration of a QRS complex in an ECG signal.

5. The device of claim 1 wherein said means for determining the presence of a QRS complex comprises:
   a) means for determining the slope of the ECG signal; and,
   b) means for generating said control signal in response to the slope found by said means for determining the slope.

6. The device of claim 5 wherein said means for determining the slope of the ECG signal includes means for determining the slope of the ECG signal over several samples.

7. The device of claim 5 wherein said means for determining the slope of the ECG signal includes means for determining the absolute value of the slope of the ECG signal.

8. The device of claim 5 wherein a plurality of ECG signals are presented to the input from a plurality of ECG leads and wherein said means for determining the slope of the ECG signal includes means for determining the maximum slope of the ECG signal determined from said plurality of ECG leads.

9. The device of claim 5 wherein said slope determination system includes:
   a) a plurality of ECG signals presented to the input from a plurality of ECG leads;
   b) means for determining the slope of the ECG signal over several samples for each ECG signal presented to the input;
   c) means for determining the absolute value of the slope determined over several samples for each ECG signal presented to the input; and,
   d) means for determining the maximum value of the absolute value of the slope determined over several samples for each ECG signal presented to the input.

10. The device of claim 5 wherein said means for generating said control signal includes:
    a) means for creating a dilation slope signal representative of the maximum value of the slope found by said means for determining the slope over a time interval approximately equal to the time length of a QRS complex on an ECG signal;
    b) means for creating a reference slope signal representing the maximum value of the slope found over a relatively long time interval by said means for determining the slope; and,
    c) means for determining a ratio of said dilation slope signal and said reference slope signal whereby a control signal is generated in response to the ratio determined by said means for determining a ratio.

11. The device as in claim 10 wherein said means for creating a reference slope signal includes:
    a) means for generating a threshold slope signal representative of the maximum slope determined by said means for determining the slope of the ECG signal over an intermediate time period;
    b) means for comparing the instantaneous slope of the ECG signal determined by said means for determining the slope to said threshold slope signal;
    c) means for decaying the value of said threshold slope if the instantaneous value of the slope found by said means for determining the slope does not become greater than the instantaneous slope within a preset time interval;
d) means for generating a reference slope signal representing the maximum slope determined by said means for determining the slope of the ECG signal over a relatively long time period; and
e) means for replacing the current value of said reference slope signal with the instantaneous slope value of the ECG signal determined by said means for determining the slope when the instantaneous slope value has a greater value than said threshold slope signal.

12. The device of claim 1 wherein said variable frequency low pass filter operates at at least three different cutoff frequencies, said filter operating at the lowest cutoff frequency during the time the ECG signal exclusive of the QRS complex is passing through said filter, said filter operating at its highest cutoff frequency during the time the ECG signal containing the QRS complex is passing through said filter, and said filter operating at cutoff frequencies between the lowest and highest cutoff frequencies for relatively short time periods so that the ECG signal output from said filter will appear relatively undistorted by the transition in cutoff frequencies from the lowest to the highest cutoff frequencies and from the highest to the lowest cutoff frequencies in response to a detection of a QRS complex by said means for determining the presence of a QRS complex.

13. A device for filtering unwanted electrical signals from an electrocardiograph (ECG) signal presented to an input comprising:
   a) a variable cutoff frequency low pass filter capable of operating at at least two different cutoff frequencies, each specific cutoff frequency enabled in response to a control signal;
   b) means, connected to the input and said low pass filter, for delaying an ECG signal presented at the input before passing the ECG signal to said low pass filter;
   c) means, connected to the input, for determining the presence of a QRS complex in the ECG signal and for creating a control signal in response thereto, said control signal having a plurality of states, each of said states corresponding to a specific cutoff frequency of said low pass filter, said control signal passed to said low pass filter, comprising:
      i) means for determining the slope of the ECG signal further comprising:
         1) a plurality of ECG signals presented to the input from a plurality of ECG leads;
         2) means for determining the slope of the ECG signal over several samples for each ECG signal presented to the input;
         3) means for determining the absolute value of the slope determined over several samples for each ECG signal presented to the input;
         4) means for determining the maximum value of the absolute value of the slope determined over several samples for each ECG signal presented to the input;
      ii) means for generating said control signal in response to the slope found by said means for determining the slope further comprising:
         1) means for creating a dilation slope signal representative of the maximum value of the slope found by said means for determining the slope over a time interval approximately equal to the time length of a QRS complex on an ECG signal;
         2) means for creating a reference slope signal representing the maximum value of the slope found over a relatively long time interval by said means for determining the slope; and,
         3) means for determining a ratio of said dilation slope signal and said reference slope signal whereby a control signal is generated in response to the ratio determined by said means for determining a ratio:
   whereby during the part of the ECG signal presented to the input not having a QRS complex, said means for determining the presence of a QRS complex and creating a control signal creates a control signal in a first state, said control signal in said first state directing said low pass filter to operate at said relatively low cutoff frequency and when a QRS complex is detected in the ECG signal by said means for determining the presence of a QRS complex, said means for determining the presence of a QRS complex and creating a control signal creates a control signal in a second state, said control signal in said second state directing said low pass filter to operate at said relatively higher cutoff frequency so that the QRS complex of the ECG signal delayed by said means for delaying is presented to said low pass filter just after said low pass filter begins operating at said relatively higher cutoff frequency, thereby passing the QRS complex through said low pass filter with relatively little attenuation.

14. A device for filtering unwanted electrical signals from an electrocardiograph (ECG) signal presented to an input comprising:
   a) a variable cutoff frequency low pass filter capable of operating at at least two different cutoff frequencies, each specific cutoff frequency enabled in response to a control signal;
   b) means, connected to the input and said low pass filter, for delaying an ECG signal presented at the input before passing the ECG signal to said low pass filter comprising an electronic memory for storing the ECG signal presented to the input for later recall;
   c) means, connected to the input, for determining the presence of a QRS complex in the ECG signal and for creating a control signal in response thereto, said control signal having a plurality of states, each of said states corresponding to a specific cutoff frequency of said low pass filter, said control signal passed to said low pass filter, comprising:
      i) means for determining the slope of the ECG signal further comprising:
         1) a plurality of ECG signals presented to the input from a plurality of ECG leads;
         2) means for determining the slope of the ECG signal over several samples;
         3) means for determining the absolute value of the slope determined over several samples;
         4) means for determining the maximum value of the absolute value of the slope determined over several samples for each ECG signal presented to the input;
      ii) means for generating said control signal in response to the slope found by said means for determining the slope further comprising:
         1) means for creating a dilation slope signal representative of the maximum value of the slope found by said means for determining the slope over a time interval approximately equal to the time length of a QRS complex on an ECG signal;

2) means for creating a reference slope signal representing the maximum value of the slope found over a relatively long time interval by said means for determining the slope comprising:

i) means for generating a threshold slope signal representative of the maximum slope determined by said means for determining the slope of the ECG signal over an intermediate time period;

ii) means for comparing the instantaneous slope of the ECG signal determined by said means for determining the slope to said threshold slope signal;

iii) means for decaying the value of said threshold slope if the instantaneous value of the slope found by said means for determining the slope does not become greater than the instantaneous slope within a preset time interval;

iv) means for generating a reference slope signal representing the maximum slope determined by said means for determining the slope of the ECG signal over a relatively long time period; and v) means for replacing the current value of said reference slope signal with the instantaneous slope value of the ECG signal determined by said means for determining the slope when the instantaneous slope value has a greater value than said threshold slope signal; and 3) means for determining a ratio of said dilation slope signal and said reference slope signal whereby a control signal is generated in response to the ratio determined by said means for determining a ratio;

whereby during the part of the ECG signal presented to the input not having a QRS complex, said means for determining the presence of a QRS complex and creating a control signal creates a control signal in a first state, said control signal in said first state directing said low pass filter to operate at said relatively low cutoff frequency and when a QRS complex is detected in the ECG signal by said means for determining the presence of a QRS complex, said means for determining the presence of a QRS complex and creating a control signal creates a control signal in a second state, said control signal in said second state directing said low pass filter to operate at said relatively higher cutoff frequency so that the QRS complex of the ECG signal delayed by said means for delaying is presented to said low pass filter just after said low pass filter begins operating at said relatively higher cutoff frequency, thereby passing the QRS complex through said low pass filter with relatively little attenuation.

15. In a device means for sensing the electrical signals of a beating heart to produce an initial ECG signal, means for processing the initial ECG signal to produce a processed ECG signal and means for providing useful information about the processed ECG signal, a system for removing unwanted electrical signals from the initial ECG signal comprising:

a) means for receiving the initial ECG signal;

b) a variable cutoff frequency low pass filter capable of operating at at least two different cutoff frequencies, each specific cutoff frequency enabled in response to a control signal;

c) means, connected to said means for receiving and said low pass filter, for delaying an ECG signal presented at said means for receiving before passing the ECG signal to said low pass filter;

d) means, connected to said means for receiving, for determining the presence of a QRS complex in the ECG signal and for creating a control signal in response thereto, said control signal having a plurality of states, each of said states corresponding to a specific cutoff frequency of said low pass filter, said control signal passed to said low pass filter;

whereby during the part of the ECG signal presented to the input not having a QRS complex, said means for determining the presence of a QRS complex and creating a control signal creates a control signal in a first state, said control signal in said first state directing said low pass filter to operate at said relatively low cutoff frequency and when a QRS complex is detected in the ECG signal by said means for determining the presence of a QRS complex, said means for determining the presence of a QRS complex and creating a control signal creates a control signal in a second state, said control signal in said second state directing said low pass filter to operate at said relatively higher cutoff frequency so that the QRS complex of the ECG signal delayed by said means for delaying is presented to said low pass filter just after said low pass filter begins operating at said relatively higher cutoff frequency, thereby passing the QRS complex through said low pass filter with relatively little attenuation.

16. A device for filtering unwanted electrical signals from an electrocardiograph (ECG) signal and for communicating the filtered ECG signal to a device to record or display the filtered ECG signal comprising:

a) means for sensing the electrical signals of a beating heart to produce an initial ECG signal;

b) means, connected to said means for sensing, for processing said initial ECG signal including:

i) a means for processing input connected to said means for sensing;

ii) a variable cutoff frequency low pass filter having a filter input and a filter output, said filter capable of operating at at least two different cutoff frequencies, each specific cutoff frequency enabled in response to a control signal;

iii) means, connected between said means for processing input and said filter input, for delaying an ECG signal presented at said means for processing input before passing the ECG signal to said filter input;

iv) means, connected to said means for processing input, for determining the presence of a QRS complex in the ECG signal and for creating a control signal in response thereto, said control signal having a plurality of states, each of said states corresponding to a specific cutoff frequency of said low pass filter, said control signal passed to said low pass filter;

v) a means for processing output connected to said filter output; whereby during the part of the ECG signal presented to the input not having a QRS complex, said means for determining the presence of a QRS complex and creating a control signal creates a control signal in a first state, said control signal in said first state directing said low pass filter to operate at said relatively low cutoff frequency and when a QRS complex is detected in the ECG signal by said means for determining the presence of a QRS complex, said means for determining the presence of a QRS complex and creating a control signal creates a control signal in a second state, said control signal in said second state directing said low pass filter to operate at said relatively higher cutoff frequency so that the QRS complex of the ECG signal delayed by said means for delaying is presented to said low pass filter just after said low pass filter begins operating at said relatively higher cutoff frequency, thereby passing the QRS complex through said low pass filter with relatively little attenuation; and, c) means, connected to said means for processing output, for communicating said filtered ECG signal to a device to record or display the filtered ECG signal.

17. A method for filtering unwanted electrical signals from an electrocardiograph (ECG) signal presented to an input comprising:

a) delaying an ECG signal presented at the input;

b) determining the presence of a QRS complex in the ECG signal presented at the input;

c) creating a control signal in response to a determination of the presence of a QRS complex;

d) operating a variable cutoff frequency low pass filter capable of operating at at least two different cutoff frequencies, the specific cutoff frequency enabled in response to said control signal, at a relatively low cutoff frequency during the part of the ECG signal presented to the input not having a QRS complex, while operating said variable cutoff frequency low pass filter at a relatively higher cutoff frequency when a QRS complex is detected in the ECG signal;

e) passing said delayed ECG signal through said variable cutoff frequency low pass filter;

whereby during the part of the ECG signal presented to the input not having a QRS complex, said low pass filter operates at a relatively low cutoff frequency and when a QRS complex is detected in the ECG signal, said control signal directs said low pass filter to operate at a relatively higher cutoff frequency so that the QRS complex of said delayed ECG signal is presented to said low pass filter just after said low pass filter begins operating in its relatively higher cutoff frequency mode, thereby passing the QRS complex through said low pass filter with relatively little attenuation.

* * * * *